US007037530B2

(12) United States Patent  
Gierer

(10) Patent No.: US 7,037,530 B2
(45) Date of Patent: May 2, 2006

(54) METHOD FOR MANUFACTURING A LOW DOSE PHARMACEUTICAL COMPOSITION HAVING UNIFORM DRUG DISTRIBUTION AND POTENCY

(75) Inventor: Daniel S. Gierer, East Lyme, CT (US)

(73) Assignee: Pfizer INC, New York, NY (US)

( * ) Notice: Subject to any disclaimer, the term of this patent is extended or adjusted under 35 U.S.C. 154(b) by 320 days.

(21) Appl. No.: 10/131,556

(22) Filed: Apr. 23, 2002

(65) Prior Publication Data

US 2003/0004182 A1    Jan. 2, 2003

Related U.S. Application Data

(60) Provisional application No. 60/287,841, filed on May 1, 2001.

(51) Int. Cl.
*A61K 9/14* (2006.01)
(52) U.S. Cl. .................. 424/489; 424/470; 514/317
(58) Field of Classification Search .............. 424/464, 424/451, 489; 514/317
See application file for complete search history.

(56) References Cited

U.S. PATENT DOCUMENTS

| 3,725,556 | A | 4/1973 | Hanssen et al. ............ 424/357 |
| 4,013,785 | A | 3/1977 | Weintraub et al. ............ 424/23 |
| 4,254,099 | A | 3/1981 | Asmussen et al. ............ 424/23 |
| 4,489,026 | A | 12/1984 | Yalkowsky ................. 264/123 |
| 5,004,613 | A | 4/1991 | Radebaugh et al. ........ 424/465 |
| 5,047,246 | A | 9/1991 | Gallian et al. .............. 424/464 |
| 5,134,127 | A | 7/1992 | Stella et al. .................. 514/58 |
| 5,376,645 | A | 12/1994 | Stella et al. .................. 514/58 |
| 5,464,632 | A | 11/1995 | Cousin et al. .............. 424/465 |
| 5,552,412 | A | 9/1996 | Cameron et al. ........... 514/317 |
| 5,733,578 | A | 3/1998 | Hunter et al. ............... 424/489 |
| 5,747,068 | A | 5/1998 | Mendizabal ................ 424/465 |
| 5,861,141 | A | 1/1999 | Mendizabal ................. 424/44 |
| 5,879,706 | A | 3/1999 | Carter et al. ................ 424/464 |
| 5,928,668 | A | 7/1999 | Greaves et al. ............. 424/489 |
| 5,976,570 | A | 11/1999 | Greaves et al. ............. 424/470 |
| 6,080,427 | A | 6/2000 | Remon ....................... 424/465 |
| 6,090,410 | A | 7/2000 | Bechard et al. ............. 424/464 |
| 6,107,331 | A | 8/2000 | MacLean et al. ........... 514/428 |
| 6,153,746 | A | 11/2000 | Shah et al. .................. 536/103 |
| 2002/0031548 | A1 * | 3/2002 | Benjamin et al. ........... 424/465 |

FOREIGN PATENT DOCUMENTS

| EP | 0503521 | 9/1992 |
| EP | 0700680 | 3/1996 |
| GB | 1570993 | 7/1980 |
| WO | WO 9716434 | 5/1997 |
| WO | WO 0115724 | 3/2001 |

OTHER PUBLICATIONS

Pharmaceutical Dosage Forms, vol. 2 Lieberman, H.A., L. Lachman, and J.B. Schwartz (Eds.), Marcel Dekker, Inc., New York, p. 40-57 (1990).
Holm, P., "Granulation in Fielder PMAT 25 MG" Department of Pharmaceutics Royal Danish School of Pharmacy) (1984).
PCT Search Report PCT/IB02/00766.

\* cited by examiner

*Primary Examiner*—Carlos A. Azpuru
*Assistant Examiner*—Eric E. Silverman
(74) *Attorney, Agent, or Firm*—Gregg C. Benson; John A. Wichtowski

(57) ABSTRACT

A method for manufacturing a pharmaceutical composition having uniform drug distribution and potency is described which utilizes silicon dioxide to reduce the loss of active ingredient during the manufacturing process. The method is particularly useful for the manufacture of low dosage tablet compositions.

27 Claims, No Drawings

US 7,037,530 B2

METHOD FOR MANUFACTURING A LOW DOSE PHARMACEUTICAL COMPOSITION HAVING UNIFORM DRUG DISTRIBUTION AND POTENCY

This application claims the benefit of U.S. Provisional Ser. No. 60/287,841 filed May 1, 2001 and incorporated herein by reference.

FIELD OF THE INVENTION

The present invention relates to a method for manufacturing a pharmaceutical composition having uniform drug distribution and potency including the compositions and medicaments produced therefrom, in particular, methods and compositions for use in the manufacture of low dosage tablet compositions containing a silicon dioxide to reduce loss of the active ingredient during the manufacturing process.

BACKGROUND

U.S. Pat No. 5,552,412 describes a class of potent and orally active selective estrogen receptor modulators (SERMS) (e.g., derivatives of tetrahydronaphthalen-2-ol) which are useful in the treatment or prevention of breast cancer, osteoporosis, obesity, cardiovascular disease, hypercholesterolemia, endometriosis and prostatic disease. These particular SERMS are of interest due to their improved oral bioavailability over current commercially available SERMS (e.g. raloxifene). The SERMS described in U.S. Pat. No. 5,552,412 are very potent thus allowing for low dosage forms. However, the formulation of compositions at the lower dose range presents a challenge in maintaining consistent potency and uniformity in the drug product manufacturing process. Of particular concern is the loss of active ingredient from adherence to or absorption onto metal surfaces to which the active SERM is exposed during the blending step (e.g., contact with metal blender blades and vessel surfaces). Although one can effectively implement a manual brushing step to recover active ingredient adhered to the metal surfaces in small scale equipment, a manual brushing step is neither efficient nor desirable in a production scale environment. Liquid processes can minimize the drug loss issues during drug product manufacturing; however, compounds that are sensitive to oxidation (e.g., tetrahydronaphthalen-2-ol derivatives) make liquid processes very difficult to perform without degradation of the active ingredient. Therefore, there is a need for an improved formulation and process that would minimize adherence of active ingredients onto metal surfaces during the manufacture of medicaments, in particular, those having a low dosage content.

SUMMARY

The present invention provides a method for manufacturing a pharmaceutical composition having uniform drug distribution and potency. The method includes (in the following order) the steps of: (1) blending silicon dioxide and at least one pharmaceutically acceptable excipient, carrier or diluent in a high shear granulator for an appropriate amount of time (about 5 minutes) to produce a blended mixture; (2) adding an active ingredient to the granulator and blending for an additional period of time (about 10 to about 15 minutes) to form an active blend; (3) transferring the active blend from the granulator to a blender; (4) optionally, adding one or more additional pharmaceutically acceptable excipients, carriers or diluents to the active blend; and (5) blending for a suitable period of time (about 5 minutes) to form a pharmaceutical composition having uniform distribution of the active ingredient and uniform potency. The resultant blended composition may then be processed further into a desired unit dosage form. In a preferred dosage form, the active ingredient is present in an amount from about 0.01 to 10.0 mg per unit dose (preferably from about 0.05 to about 5.0 mg, more preferably from about 0.05 to about 4.0 mg, even more preferably from about 0.1 to about 3.5 mg, and most preferably from about 0.1 to about 2.5 mg per unit dose) and the silicon dioxide is present in an amount from about 0.1 to about 2% by weight of the unit dosage form (more preferably from about 0.15 to about 1.0% by weight of the unit dosage form and most preferably from about 0.25 to about 0.75% by weight of the unit dosage form).

In another embodiment of the present invention, a pharmaceutical composition is provided that is prepared using the method described above. In particular, a low dosage pharmaceutical composition is provided that comprises an active ingredient (preferably lasofoxifene), a silicon dioxide, and at least one pharmaceutically acceptable excipient, carrier, or diluent wherein the active ingredient is present in an amount less than 4.0% w/w active ingredient (more preferably $\geq$ about 0.01% w/w active ingredient and <4% w/w active ingredient, even more preferably $\geq$ about 0.01% w/w active ingredient and $\leq$ about 3.5% w/w active ingredient, most preferably $\geq$ about 0.1% w/w active ingredient and $\leq$ about 2.5% w/w active ingredient) and the silicon dioxide is present in an amount from about 0.1 to about 2 weight percent.

In yet another embodiment of the present invention, a medicament is provided that is prepared by the method described above into a unit dosage form, in particular a low dosage form.

DEFINITIONS

As used herein, the term "uniform distribution" refers to a blended mixture which meets the FDA criteria (Guidance for Industry ANDA's: Blend Uniformity Analysis, published August 1999) of 10 individual blend samples achieving 90–110% potency of the theoretical strength with an RSD of <5% for all blend samples.

The term "uniform potency" refers to a blended mixture that maintains a drug substance activity level greater than or equal to about 90% throughout the manufacturing process.

The phrase "pharmaceutically acceptable" indicates that the substance or composition must be compatible chemically and/or toxicologically, with the other ingredients comprising a formulation, and/or the mammal being treated therewith.

The term "active ingredient" refers to a therapeutically active compound, as well as any prodrugs thereof and pharmaceutically acceptable salts, hydrates and solvates of the compound and the prodrugs.

The term "appropriate period of time" or "suitable period of time" refers to the period of time necessary to achieve a desired effect or result. For example, a mixture may be blended until a potency distribution is reached that is within an acceptable qualitative range for a given application or use of the blended mixture.

As used herein, the term "unit dose" or "unit dosage" refers to a physically discrete unit that contains a predetermined quantity of active ingredient calculated to produce a desired therapeutic effect. The unit dose or unit dosage may be in the form of a tablet, capsule, sachet, etc. referred to herein as a "unit dosage form."

DETAILED DESCRIPTION

The present invention provides a process for maintaining uniformity and potency during the manufacture of a pharmaceutical composition containing a highly potent active ingredient. The process includes a means for reducing the loss of active ingredients that adhere to the metal surfaces of equipment during the manufacturing process of a pharmaceutical composition or medicament. Active ingredients of particular interest are SERM compounds of Formula (I) below:

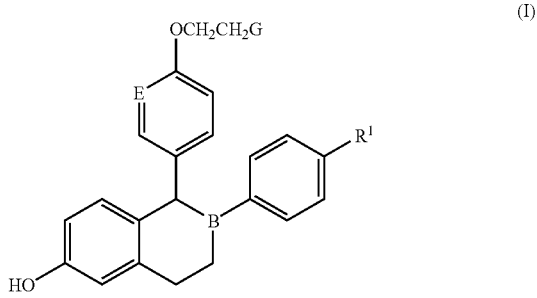

where E and B are independently selected from CH and N; $R^1$ is hydrogen, hydroxy, fluoro or chloro; and G is

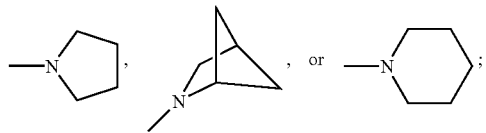

a prodrug thereof, or a pharmaceutically acceptable salt, hydrate or solvate of the compound or the prodrug.

Preferred compounds include cis-6-(4-fluoro-phenyl)-5-[4-(2-piperidin-1-yl-ethoxy)-phenyl]-5,6,7,8-tetrahydro-naphthalen-2-ol; (−)-cis-6-phenyl-5-[4-(2-pyrrolidin-1-yl-ethoxy)-phenyl]-5,6,7,8-tetrahydro-naphthalen-2-ol; cis-6-phenyl-5-[4-(2-pyrrolidin-1-yl-ethoxy)-phenyl]-5,6,7,8-tetrahydro-naphthalen-2-ol; cis-1-[6'-pyrrolodinoethoxy-3'-pyridyl]-2-phenyl-6-hydroxy-1,2,3,4-tetrahydrohaphthalen-1-(4'-pyrrolidinoethoxyphenyl)-2-(4''-fluorophenyl)-6-hydroxy-1,2,3,4-tetrahydroisoquinoline; cis-6-(4-hydroxyphenyl)-5-[4-(2-piperidin-1-yl-ethoxy)-phenyl]-5, 6,7,8-tetrahydro-naphthalen-2-ol; and 1-(4'-pyrrolidinolethoxyphenyl)-2-phenyl-6-hydroxy-1,2,3,4-tetrahydroisoquinoline. A more preferred compound is cis-6-phenyl-5-[4-(2-pyrrolidin-1-ylethoxy)phenyl]-5,6,7,8-tetrahydronaphthalen-2-ol; a prodrug thereof, or a pharmaceutically acceptable salt, hydrate or solvate of the compound or the prodrug.

The compounds of Formula (I) are very potent compounds thus requiring special handling to reduce operator exposure during the manufacturing process. In addition, the compounds of Formula (I) may be sensitive to oxidation which may limit or preclude the use of liquids and materials containing peroxide contaminants (e.g., polyethylene glycols) during drug product manufacture. Conventional methods for manufacturing tablets typically use a wet or dry granulation step prior to compression into a tablet.

The types of mixing processes for a dry granulation can be divided into two broad categories: (i) batch, and (ii) continuous. The most prevalent type used in the pharmaceutical industry is the batch type which mixes a sub-lot or total lot of a formulation at one time. In a batch-type mixer, particle movement is achieved by rotation of the entire mixer shell or body. For schematics and a description of the different types of batch-type mixers, see *Pharmaceutical Dosage Forms*, Vol. 2, Lieberman, H. A., L. Lachman, and J. B. Schwartz (Eds.), Marcel Dekker, Inc., New York, pp 40–57 (1990).

In a Blend/Mill/Blend dry granulation process, the following steps are generally employed:

(1) pass an active ingredient through an appropriately sized sieve and then blend in a blender (e.g., twin shell blender) for an appropriate period of time to produce a blended mixture;

(2) filter an excipient blend through an appropriately sized sieve and add a portion of the filtered excipient blend to the blender containing the active ingredient;

(3) blend the mixture for an appropriate period of time;

(4) filter the active blend through an appropriately sized screen;

(5) charge a blender with half of the remaining filtered excipient blend followed by the filtered active blend from step (4);

(6) blend the mixture for an appropriate period of time;

(7) add the remaining filtered excipient blend to the active mixture and blend for an appropriate period of time;

(8) filter the blended mixture from step (7) through a mill;

(9) blend the active mixture from step (8) for an appropriate period of time in a blender; and

(10) add any additional excipients, carriers or diluents and blend until an acceptable distribution of materials is achieved.

The conventional blend/mill/blend dry process presents several disadvantages. For example, it is labor intensive, the dusty operation increases the operator's exposure to the active ingredient, and the increased exposure to metal surfaces increases the risk of potency loss. In addition, segregation problems are observed with mixtures having wide particle size distribution and large differences in particle densities. Tumbling-type blenders are generally not suitable for fine particulate systems because there may not be enough shear to reduce particle agglomeration and, if the powders are free flowing, serial dilution may be required for the addition of low dose active ingredients.

When the dry granulation process described above was used to blend a formulation containing a compound of Formula (I), a non-uniform distribution of potency was observed across the granulation particles. Although the potential for operator exposure to the active ingredient is greatly reduced in a conventional wet granulation process, the active ingredient is exposed to liquids and dissolved oxygen during the process which increases the potential for oxidation of the compound. Attempts to reduce the chemical instability of the compound of Formula (I) in a wet granulation process have not been successful. However, Applicant discovered that the use of high shear wet process blending equipment adapted for use as a dry process addressed both the operator exposure to the drug and reduced degradation of the active ingredient due to oxidation observed during the conventional dry and wet granulation processes.

High speed granulators are stationary shell mixers with a large mixer-scraper blade that mixes the ingredients, eliminates dead spots in the mixer container and presents the mixer contents to a high-speed chopper blade which intimately mixes the ingredients. The equipment is extremely rapid and provides intimate solids/solids mixing. In a vertical type of mixer (e.g., equipment available from LÖDIGE Industries, Paderborn, Germany; NIRO Inc., Columbia, Md.; and DIOSNA Dierks & Soehne GmbH, Osnabrueck, Germany), rotating mixing impellers mix the particles centrifugally at high speed causing a highly fluidized vortex of material. A chopper, rotating at a very high speed, interrupts the ascending circulation of the material and diverts the product into a vertical flow. For a more detailed description, see Record, P. C., *Manuf. Chem. Aerosol. News,* 50, 65 (1979). Other suitable high-speed granulators include Spectrum™ and Pharma Matrix™ (both available from Niro Pharma Systems, Columbia, Md.).

The present invention provides a dry process that comprises the following steps:

(1) blending at least one pharmaceutically acceptable excipient, carrier or diluent in a high shear granulator for an appropriate amount of time;
(2) adding an active ingredient to the granulator and blending for an additional period of time to form an active blend;
(3) transferring the active blend from the granulator to a blender;
(4) optionally, adding one or more additional pharmaceutically acceptable excipients, carriers or diluents to the mixture; and
(5) blending for a suitable period of time to form a final pharmaceutical composition having a uniform distribution of the active ingredient in the composition.

The final pharmaceutical composition is processed into a unit dosage form (e.g., tablet, capsule or sachet) and then packaged for distribution. The processing step will vary depending upon the particular unit dosage form. For example, a tablet is generally compressed under pressure into a desired shape and a capsule or sachet employs a simple fill operation. Those skilled in the art are well aware of the procedures used for manufacturing the various unit dosage forms.

The active blend generally includes one or more pharmaceutically acceptable excipients, carriers or diluents. The particular carrier, diluent or excipient used will depend upon the means and purpose for which the active ingredient is being applied. In general, a tablet formulation includes materials such as diluents, binders, lubricants, disintegrants and mixtures thereof. Suitable diluents include various types of starch, lactose, mannitol, kaolin, calcium phosphate or sulfate, inorganic salts (e.g., sodium chloride), powdered sugar, and powdered cellulose derivatives. To ensure content uniformity of the blend, a volume mean diameter drug substance particle size of less than or equal to about 30 microns is preferably utilized. Preferred diluents are microcrystalline cellulose (e.g., Avicel® PH102 or PH101 available from FMC Pharmaceutical, Philadelphia, Pa.) and lactose. The mean particle size for the microcrystalline cellulose generally ranges from about 90 μm to about 200 μm. Suitable grades of lactose include anhydrous lactose (about 152 μm mean), lactose monohydrate and spray dried lactose (e.g., Fast Flo™ lactose, about 87 μm mean, available from Foremost Corp., Baraboo, Wis.).

If desired, a binder may be added. Suitable binders include substances such as celluloses (e.g., cellulose, methylcellulose, ethylcellulose, and hydroxymethylcellulose), polypropylpyrrolidone, polyvinylprrolidone, gelatin, gum arabic, polyethylene glycol, starch, sugars (e.g., lactose, sucrose, fructose, and glucose), natural and synthetic gums (e.g., acacia, alginates, and gum arabic) and waxes.

A lubricant is typically used in a tablet formulation to prevent the tablet and punches from sticking in the die. Suitable lubricants include slippery solids such as talc, magnesium and calcium stearate, stearic acid, light anhydrous silicic acid, and hydrogenated vegetable oils. A preferred lubricant is magnesium stearate.

Disintegrants may also be added to the composition to break up the dosage form and release the compound. Suitable disintegrants include starches (e.g., corn or potato starches and hydroxypropylstarch), clays, celluloses (e.g., cellulose, wood cellulose, methyl- or ethyl-cellulose, low substituted hydroxypropylcellulose, and carboxymethylcellulose), agar, algins (e.g., alginic acid), powdered natural sponge, cation-exchange resins, citrus pulp, bentonite, sodium bicarbonate, calcium phosphate, calcium citrate, sodium lauryl sulfate, and gums (e.g., guar gum).

Other useful additives include materials such as agents for retarding dissolution (e.g., paraffin), resorption accelerators (e.g., quaternary ammonium compounds), surface active agents (e.g., cetyl alcohol, glycerol monostearate, and sodium lauryl sulfate), adsorptive carriers (e.g., kaolin and bentonite), preservatives, sweeteners, coloring agents, flavoring agents (e.g., citric acid, menthol, glycine or orange powder), stabilizers (e.g., citric acid or sodium citrate), binders (e.g., hydroxypropylmethylcellulose), and mixtures thereof.

There is a great deal of flexibility in the order of addition of components into the high shear granulator for the initial blending step. Preferably, the drug substance is not added to the high shear bowl first. The typical blending time for the blending in the high shear granulator is from about 10 minutes to about 15 minutes. Although blending times greater than 15 minutes can be used, care should be taken not to demix the blend. The granulator impeller speed is typically run at about 55% to about 65% unit capacity and the chopper is preferably run at the slowest speed setting. Excessive impeller speeds could lead to fluidization of the blend and produce a blend potency loss.

After the high shear blending step, the active blend is blended in a twin shell "V" or bin blender. The typical blending time is about 5 minutes, although small scale lots have been successfully blended up to about 15 minutes. The lubricant is then added to the active blend and blended for about 5 minutes in the twin shell "V" or bin blender.

The process described above provides efficient mixing and a more uniform distribution of the active ingredient without significant degradation of the active ingredient; however, the loss of active ingredient due to adherence or attraction of the compound to the metal surfaces of the equipment (e.g., blades and vessel surfaces) presented an additional challenge especially for low dosage formulations (e.g., less than 4 mg per unit dose). The addition of a glidant such as talc did not resolve the problem. Although the addition of talc to the formulation reduced the loss of active ingredient in the blending process (potency increase from 77.2% to 91.0% of the blended composition), talc did not completely prevent adhesion to the metal surface. When a manual brushing step was implemented after blending the talc formulation, an increase in potency to 96.8% was observed which indicates that about 5% to about 6% of the active ingredient is still adhering to the metal surface. A 5–6% loss of a very potent active ingredient, such as the compounds of Formula (I), is significant. However, when silicon dioxide (e.g., Syloid™ 244FP available from W. R. Grace, Columbia, Md.) was added to the formulation, an increase of potency from 77.2% to 96.3% of the blended composition was is observed without the addition of a manual brushing step.

Although the addition of silicon dioxide to pharmaceutical formulations have been utilized to improve the flow of powder blends and minimize tablet weight variation, the incorporation of $SiO_2$ (as observed above) unexpectedly and surprisingly reduced the loss of active ingredient due to absorption or adherence to the metal surfaces of the process equipment. A variety of silicon dioxides are available from a number of commercial vendors and are well known to those skilled in the art. A particularly useful silicon dioxide is colloidal silicon dioxide which is a submicron fumed silica prepared by the vapor-phase hydrolysis of a silicon compound, such as silicon tetrachloride. Colloidal silica is an amorphous powder which is available commercially from a number of sources, including Cabot Corporation, Boston, Mass. (Cab-O-Sil™); Degussa, Inc., Düsseldorf, Germany (Aerosil™); E.I. DuPont & Co., Wilmington, Del.; and W. R. Grace & Co., Columbia, Md. (Syloid™). Colloidal silicon dioxide is also known as colloidal silica, fumed silica, light anhydrous silicic acid, silicic anhydride, and silicon dioxide fumed, among others. A variety of commercial grades of colloidal silicon dioxide are produced by varying the manufacturing process. These modifications do not affect the silica content, specific gravity, refractive index, color or amorphous form. However, these modifications are known to change the particle size, surface areas, and bulk densities of the colloidal silicon dioxide products. The mean particle size for the silicon dioxide is generally less than or equal to about 15 μm/bulk density (less than or equal to about 21.0 lbs./ft$^3$(336 kg/m$^3$)). Preferably, the silicon dioxide is in the form of a dry powder and not a liquid suspension.

The silicon dioxide is generally present in an amount from about 0.1 to about 2% by weight of the dosage form, preferably, in an amount from about 0.15 to about 1.0% by weight and most preferably in an amount from about 0.25 to about 0.75% by weight of the dosage form.

Procedures for making compounds of Formula (I) are described in U.S. Pat. No. 5,552,412, incorporated herein by reference, and the resolution of racemic mixtures is described in WO97/16434. The active ingredient may be used per se or in the form of its pharmaceutically acceptable salt, solvate and/or hydrate. The term "pharmaceutically acceptable salt" refers to non-toxic acid addition salts derived from inorganic and organic acids. Suitable salt derivatives include halides, thiocyanates, sulfates, bisulfates, sulfites, bisulfites, arylsulfonates, alkylsulfates, phosphonates, monohydrogen-phosphates, dihydrogenphosphates, metaphosphates, pyrophosphonates, alkanoates, cycloalkylalkanoates, arylalkonates, adipates, alginates, aspartates, benzoates, fumarates, glucoheptanoates, glycerophosphates, lactates, maleates, nicotinates, oxalates, palmitates, pectinates, picrates, pivalates, succinates, tartarates, citrates, camphorates, camphorsulfonates, digluconates, trifluoroacetates, and the like. A preferred salt of compounds of Formula (I) is tartrate (in particular, D-tartrate) or citrate. A preferred compound is lasofoxifene (cis6-phenyl-5-[4-(2-pyrrolidin-1-ylethoxy)phenyl]-5,6,7,8-tetrahydronaphthalen-2-ol). The active ingredient is generally present in a pharmaceutical composition in an amount less than or equal to about 10% w/w. For a low dosage application, the active ingredient is typically present in the pharmaceutical composition in an amount less than 4.0% w/w active ingredient, more preferably ≧about 0.01% w/w active ingredient and <4% w/w active ingredient, even more preferably ≧about 0.01% w/w active ingredient and ≦about 3.5% w/w active ingredient, most preferably ≧about 0.1% w/w active ingredient and ≦about 2.5% w/w active ingredient).

The pharmaceutical composition can be used to produce unit dosage forms containing about 0.05 mg to about 10.0 mg active ingredient per unit dosage, preferably, about 0.1 mg to about 5.0 mg active ingredient per unit dosage. The tablet size (i.e., unit dosage form) is typically between about 100 mg and 600 mg. As used herein, "low dosage form" refers to a unit dose containing less than about 5.0 mg active ingredient. A typical low dosage form contains between about 0.01 and about 5.0 mg active ingredient, preferably between about 0.05 mg and about 4.0 mg, more preferably between about 0.1 mg and about 3.5 mg, most preferably between about 0.1 mg and 2.5 mg.

For example, the tablet formulation for a 0.25 mg, 0.1 mg and 0.05 mg tablet typically consists of a blend containing about 0.14% w/w active ingredient and the tablet size is varied to achieve the proper dosage; whereas, a 0.5 mg tablet formulation generally contains a blend having about 0.68% w/w active ingredient. The concentration of active ingredient in the final pharmaceutical composition is generally adjusted by increasing or decreasing the amount of diluent (e.g., lactose) added to the formulation.

The tablets are generally prepared by compression in a rotary press. However, the particular method used for tablet formation is non-limiting and is well known to those skilled in the art. After formation of the tablets, the tablets are often coated with one or more coatings. The tablet may be coated with a coating to mask flavor, to act as a sealant and/or to act as a receptor for printing a logo or trademark on the tablet surface. A common coating is a sugar coating (e.g., sucrose or sorbitol coating). Alternatively, the tablet may be coated with a film-forming protecting agent(s) to modify the dissolution properties of the tablet. For example, the tablet may be coated with a film-forming coating that resists dissolution for a predictable period of time thus resulting in a delayed or prolonged release of the active ingredient. Suitable film-forming protecting agents include celluloses (e.g., hydroxypropyl-methylcellulose, hydroxypropyl cellulose, methylcellulose), polyvinyl pyrrolidone, and ethyl acrylate-methyl methacrylate copolymers. The coating formulations may also include additives such as solubilizing agents (e.g., triacetin), preservatives, sweeteners, flavoring agents, coloring agents and other known additives to provide an elegant presentation of the drug. The compounds may also be formulated as chewable tablets, by using large amounts of pleasant-tasting substances such as mannitol in the formulation.

Alternatively, the active pharmaceutical blend may be filled into capsules. The particular capsule or method used to fill the capsule are not limiting and are well known to those skilled in the pharmaceutical manufacturing arts.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The pharmaceutical compositions containing the compounds of Formula (I) described herein are useful in the treatment or prevention of, inter alia, breast cancer, osteoporosis, obesity, cardiovascular disease, hypercholesterolemia, endometriosis and prostatic disease. Accordingly, the pharmaceutical formulations and processes described herein containing the compounds of Formula (I) may be used in the manufacture of a medicament for the therapeutic applications described above. A therapeutically effective amount of the manufactured medicament may be administered to a human in need of such treatment or prevention. As used herein, the term "therapeutically effective amount" refers to an amount of active ingredient which is capable of inhibiting or preventing the various pathological conditions or symptoms thereof and sequelae, referred to above. The terms "inhibit" or "inhibiting" refers to prohibiting, treating, alleviating, ameliorating, halting, restraining, slowing or reversing the progression, or reducing the severity of a pathological condition or symptom related to or resultant from the respective condition being treated. As such, the pharmaceutical formulations may be used for both medical therapeutic (acute or chronic) and/or prophylactic (prevention) administration as appropriate. The dose, frequency and duration will vary depending on such factors as the nature and severity of the condition being treated, the age and general health of the host and the tolerance of the host to the active ingredient. The pharmaceutical composition or medicament may be given in a single daily dose or in multiple doses during the day. The regimen may last from about 2–3 days to several weeks or longer. Typically, the composition is administered to a human patient once to four times a day with a unit dosage of about 0.05 mg to about 50 mg, but the above dosage may be properly varied depending on the age, body weight and medical condition of the patient and the type of administration. A preferred dosing regimen for a human patient is a daily administration of about 0.25 mg per kg to about 25 mg per kg.

The following Examples illustrate the preparation of compounds of Formula (I) and their use in pharmaceutical compositions and manufacturing processes of the present invention. Although a particular SERM compound (lasofoxifene) is used to illustrate the invention, it will be understood by those skilled in the art that the inventive process can be used for any compound that would benefit from increased uniformity of potency and distribution of the active ingredient in a pharmaceutical composition by means of the present invention. The examples are not intended to be limiting to the scope of the invention in any respect, and should not be so construed.

EXAMPLES

Preparation of cis-6-phenyl-5-[4-(2-pyrrolidin-1-ylethoxy)phenyl]-5,6,7,8-tetrahydronaphthalen-2-ol ("lasofoxifene")

Lasofoxifene was prepared as described in U.S. Pat. No. 5,552,412 and reproduced below.

A solution of 1-[2-[4-(6-methoxy-2-phenyl-3,4 dihydronaphthalen-1-yl)phenoxy]ethyl]pyrrolidine hydrochloride (nafoxidene hydrochloride) (1.0 g, 2.16 mmol) in 20 mL of absolute ethanol containing 1.0 g of palladium hydroxide on carbon was hydrogenated at 60 psi (0.41 MPa) at 20° C. for 19 hr. Filtration and evaporation provided 863 mg (93%) of cis-1-{2-[4-(6-methoxy-2-phenyl 1,2,3,4-tetrahydronaphthalen-1-yl)phenoxy] ethyl}pyrrolidine.

$^1$H-NMR (CDCl$_3$.): δ 3.50–3.80 (m, 3H), 3.85 (s, 3H), 4.20–4.40 (m, 3H), 6.80–7.00 (m, 3H); MS 428 (P$^{+1}$).

To a solution of 400 mg (0.94 mmol) of cis-1-{2-[4-(6-methoxy-2-phenyl 1,2,3,4-tetrahydronaphthalen-1-yl)phenoxy] ethyl} pyrrolidine in 25 mL of methylene chloride at 0° C. was added, dropwise with stirring, 4.7 ml (4.7 mmol) of a 1.0 M solution of boron tribromide in methylene chloride. After 3 hours at room temperature, the reaction was poured into 100 mL of rapidly stirring saturated aqueous sodium bicarbonate. The organic layer was separated, dried over sodium sulfate, filtered, and concentrated to afford 287 mg (74% yield) of lasofoxifene as the free base.

$^1$H-NMR (CDCl$_3$): δ 3.35 (dd, 1H), 4.00 (t, 2H), 4.21 (d, 1H), 6.35 (ABq, 4H). The corresponding hydrochloride salt was prepared by treating a solution of the base with excess 4N HCl in dioxane, followed by evaporation to dryness and ether trituration (MS: 415 [P$^{+1}$]).

Alternatively, lasofoxifene may be prepared using the procedures described below.

Preparation of 1-[2-[4-(6-methoxy-3,4-dihydronaphthalen-1-yl)phenoxy]ethyl]pyrrolidine: A mixture of anhydrous CeCl$_3$ (138 g, 560 mmol) and THF (500 mL) was vigorously stirred for 2 h. In a separate flask, a solution of 1-[2-(4-bromophenoxy)ethyl]pyrrolidine (100 g, 370 mmol) in THF (1000 mL) was cooled to −78° C. and n-BuLi (2.6 M in hexanes, 169 mL, 440 mmol) was slowly added over 20 min. After 15 min, the solution was added to the CeCl$_3$ slurry cooled at −78° C. via cannula and the reaction was stirred for 2 h at −78° C. A solution of 6-methoxy-1-tetralone (65.2 g, 370 mmol) in THF (1000 mL) at −78° C. was added to the arylcerium reagent via cannula. The reaction was allowed to warm slowly to room temperature and was stirred for a total of 16 h. The mixture was filtered through a pad of Celite™. The flitrate was concentrated in vacuo and 3 N HCl (500 mL) and Et$_2$O (500 mL) were added. After stirring for 15 min, the layers were separated. The aqueous layer was further washed with Et$_2$O (2×). The combined organic layers were dried (MgSO$_4$), filtered, and concentrated to provide 6-methoxy-1-tetralone (22 g). The aqueous layer was basified to pH 12 with 5 N NaOH and 15% aqueous (NH$_4$)$_2$CO$_3$ (1000 mL) was added. The aqueous mixture was extracted with CH$_2$Cl$_2$ (2×). The organic solution was dried (MgSO$_4$), filtered, and concentrated to provide a brown oil. Impurities were distilled off (110°–140° C. @ 0.2 mmHg) to yield the product (74 g, 57%).

$^1$H NMR (250 MHz, CDCl$_3$): δ 7.27 (d, J=8.7 Hz, 2H), 6.92–6.99 (m, 3H), 6.78 (d, J=2.6 Hz, 1H), 6.65 (dd, J=8.6, 2.6 Hz, 1H), 5.92 (t, J=4.7 Hz, 1H), 4.15 (t Hz, 2H), 3.80 (s, 3H), 2.94 (t, J=6.0 Hz, 2H), 2.81 (t, J=7.6 Hz, 2H), 2.66 (m, 2H), 2.37 (m, 2H), 1.84 (m, 4H).

Preparation of 1-[2-[4, (2-bromo-6-methoxy-3,4-dihydronaphthalen-1-yl)phenoxy]ethyl]pyrrolidine: Pyridinium bromide perbromide (21.22 g, 60.55 mmol) was added portionwise to a solution of 1-{2-[4-(6-methoxy-3,4-dihydronaphthalen-1-yl)phenoxy]ethyl]pyrrolidine (23 g, 72 mmol) in THF (700 mL). The reaction was stirred for 60 h. The precipitate was filtered through a Celite pad with the aid of THF. The off-white solid was dissolved in CH$_2$Cl$_2$ and MeOH and was filtered away from the Celite. The organic solution was washed with 0.5 N aq HCl followed by saturated NaHCO$_3$ (aq). The organic solution was dried (MgSO$_4$), filtered, and concentrated to provide a brown solid (21.5 g, 83%).

$^1$H NMR (250 MHz, CDCl$_3$): δ 7.14 (d, J=8.7 Hz, 2H), 6.97 (d, J=8.8 Hz, 2H), 6.71 (d, J=2.2 Hz, 1H), 6.55 (m, 2H), 4.17 (t, J=6.0 Hz, 2H), 3.77 (s, 3H), 2.96 m,(4H), 2.66 (m, 4 H), 1.85 (m, 4H).

Preparation of 1-{2-[4-(6-methoxy-2-phenyl-3,4-dihydronaphthalen-1yl)phenoxy]ethyl]pyrrolidine hydrochloride (Nafoxidene hydrochloride): To a mixture of 1 [2-[4-(2-bromo-6-methoxy-3,4-dihydronaphthalen-1-yl)

phenoxy]ethyl}pyrrolidine (19 g, 44 mmol), phenylboronic acid (7.0 g, 57 mmol), and tetrakis(triphenylphosphonium) palladium (1.75 g, 1.51 mmol) in THF (300 mL) was added $Na_2CO_3$ (13 g, 123 mmol) in $H_2O$ (100 mL). The reaction was heated at reflux for 18 h. The layers were separated and the organic layer was washed with $H_2O$ followed by brine. The organic solution was dried ($MgSO_4$), filtered, and concentrated to yield 17.96 g of a brown solid. The residue was dissolved in a 1:1 mixture of $CH_2Cl_2$ and EtOAc (250 mL) and 1 N HCl in $Et_2O$ (100 mL) was added. After stirring for 2 h, product was allowed to crystallize from solution and 11 g of material was collected by filtration. Concentration of the mother liquor to half its volume provided an additional 7.3 g of product.

Preparation of cis-1-[2-[4-(6-methoxy-2-phenyl-1,2,3,4-tetrahydro-naphthalen-1yl)phenoxy]ethyl]pyrrolidine: 1-[2-[4-(6-Methoxy-2-phenyl-3,4-dihydronaphthalen 1yl)phenoxy]ethyl]pyrrolidine hydrochloride (nafoxidene hydrochloride) (75 g, 162 mmol) was dissolved in 1000 mL of EtOH and 300 mL of MeOH. Dry $Pd(OH)_2$ on carbon was added and the mixture was hydrogenated on a Parr shaker at 50° C. and 50 psi (0.34 MPa) for 68 h. The catalyst was filtered off with the aid of Celite and the solvents were removed in vacuo. The resulting white solid was dissolved in $CH_2Cl_2$ and the solution was washed with saturated $NaHCO_3$ (aq). The organic solution was dried ($MgSO_4$), filtered, and concentrated to yield an off-white solid (62.6 g, 90%).

Preparation of cis-6-phenyl-5-[4-(2-pyrrolidin-1-ylethoxy)phenyl]-5,6,7,8-tetrahydronaphthalene-2-ol: A mixture of cis-1-[2-[4-(6-methoxy-2-phenyl-1,2,3,4 tetrahydronaphthalen-1-yl)phenoxy] ethyl}pyrrolidine (12 g, 28 mmol), acetic acid (75 mL), and 48% HBr (75 mL) was heated at 100° C. for 15 h. The solution was cooled and the resulting white precipitate was collected by filtration. The hydrobromide salt (9.6 g, 69%) was dissolved in $CHCl_3$/MeOH and was stirred with saturated $NaHCO_3$ (aq). The layers were separated and the aqueous layer was further extracted with $CHCl_3$/MeOH. The combined organic layers were dried ($MgSO_4$), filtered, and concentrated to yield product as an off-white foam.

$^1$H NMR (250 MHz, $CDCl_3$): δ 7.04 (m, 3H), 6.74 (m, 2H), 6.63 (d, J=8.3 Hz, 2H), 6.50 (m, 3H), 6.28 (d, J=8.6 Hz, 2H), 4.14 (d, J=4.9 Hz, 1H), 3.94 (t, J=5.3 Hz, 2H), 3.24 (dd, J=12.5, 4.1 Hz, 1H), 2.95 (m, 4H), 2.14 (m, 1H), 1.88 (m, 4H), 1.68 (m, 1H).

The following example compares a conventional wet granulation process and a solution wet granulation process with the present invention (dry granulation process).

Example 1

The following materials used in Example 1 may be obtained from the corresponding sources listed below:

| | |
|---|---|
| Avicel ™ PH101 (microcrystalline cellulose) | FMC Pharmaceutical (Philadelphia, PA) |
| Lactose Fast Flo ™ 316 | Foremost Corp. (Baraboo, WI) |
| magnesium stearate | Mallinckrodt (St. Louis, MO) |
| hydroxypropyl cellulose | Hercules Inc. (Hopewell, VA) |
| sodium croscarmellose | FMC Pharmaceutical (Philadelphia, PA) |
| β-cyclodextrin sulfobutyl ether | Prepared using the method described in U.S. Pat. No. 6,153,746 |
| silicon dioxide ProSolv ™ 50 (silicified microcrystalline cellulose) | Grace Davison (Columbia, MD) Penwest, Patterson, NJ |

Lasofoxifene Conventional Wet Granulation Process (Comparative Process)

The following ingredients were added to a high shear blender in the listed order.

| | |
|---|---|
| lactose | 5.000 g |
| microcrystalline cellulose | 17.432 g |
| sodium croscarmellose | 1.000 g |
| hydroxypropyl cellulose | 1.250 g |
| silicon dioxide | 0.125 g |
| Lasofoxifene | 0.068 g |

The mixture was blended for approximately 15 minutes. While blending, an appropriate amount of water (approximately 63% w/w of dry blend) was added over a 8.5 minute period and then allowed to continue blending for an additional 30 seconds to achieve the desired wet mass. The wet mass was then dried to a moisture level less than about 2% under vacuum (about 50 millibar (mB)). The dried granulation was milled through a conical mill fitted with a 0.04 inch (0.10 cm) screen and round edge impeller set at 1750 rpm speed. The mixture was blended for about 10 minutes in a 150 cc glass bottle on a Turbula mixer. Magnesium stearate (0.125 g) was added to the mixture and then blended for about 5 minutes. The active blend was then compressed into tablets using a Kilian™ T100 tablet press (available from Kilian & Co., Inc., Horsham, Pa.).

Lasofoxifene Drug In Solution Wet Granulation Process (Comparative Process)

Water (100 mL) was added to a 250 mL glass beaker equipped with a mixer. While stirring, β-cyclodextrin sulfobutyl ether (0.452 g) was added followed by the lasofoxifene (0.113 g) and allowed to stir until the β-cyclodextrin sulfobutyl ether and lasofoxifene dissolved and a solution was formed. The following ingredients were then added in the order listed into a high shear blender.

| | |
|---|---|
| lactose | 5.000 g |
| silicified microcrystalline cellulose | 17.540 g |
| sodium croscarmellose | 1.000 g |
| hydroxypropyl cellulose | 1.250 g |

The mixture was blended for about 2 minutes. While blending, the lasofoxifene:water solution was added over a 3 minute period. The wet mass was then dried to a moisture level of less than about 1% in a 50° C. forced hot air oven. The dried granulation was passed through a conical mill fitted with a 0.055 inch (0.14 cm) screen and round edge impeller set at 1750 rpm speed. Magnesium stearate (0.125 g) was added to the mixture and then blended for about 5 minutes. The active blend was then compressed into tablets using a Manesty™ F-Press tablet press (available from Thomas Engineering Inc., Hoffman Estates, Ill.).

Lasofoxifene Dry Granulation Process

The following ingredients were added in the order listed into a high shear blender

| | |
|---|---:|
| lactose | 1052.25 g |
| microcrystalline cellulose | 375.00 g |
| croscarmellose sodium | 45.00 g |
| silicon dioxide | 7.50 g |
| Lasofoxifene | 5.25 g |

The lactose, microcrystalline cellulose, croscarmellose sodium and silicon dioxide were blended for 5 minutes. The lasofoxifene was added next and blended for about 15 minutes. The active blend was then discharged from the high shear blender and blended for about 5 minutes in a twin shell "V" blender. Magnesium stearate (7.50 g) was added to the active blend and blended for about 5 minutes. The active blend was roller compacted on a Vector Freund™ roller compactor unit and milled through a rotating granulator fitted with a 0.033" (0.084 cm) screen (both available from Vector Corp., Marion, Iowa). The active granulation was blended for about 5 minutes in a twin shell "V" blender. Another portion of magnesium stearate (7.50 g) was added to the granulation and blended for about 5 minutes. The final blend was compressed into tablets on a Kilian™ 100 rotary press.

Table 1 below summarizes the stability results by high pressure liquid chromatography observed for the three different processes.

TABLE I

Comparison of Lasofoxifene Stability

| Manufacturing Process | Dry Granulation | Conventional Wet Granulation (comparative) | Drug In Solution Wet Granulation (comparative) |
|---|---|---|---|
| Percent Drug Load | 0.14 | 0.28 | 0.068 |
| Total Percent Initial Impurities | 0.02 | Not Available | 0.95 |
| Total Percent Impurities at 5° C. | 0.13 at 12 months | 0.54 at 6 weeks | 1.43 at 6 weeks |
| Total Percent Impurities at 30° C. | 0.13 at 12 months | 1.21 at 6 weeks | 2.03 at 6 weeks |
| Total Percent Impurities at 40° C./75% RH | 0.41 at 6 months | 4.3 at 6 weeks | 3.10 at 6 weeks |
| Total Percent Impurities at 50° C. | 0.39 at 6 months | 5.26 at 6 weeks | 4.25 at 6 weeks |

What is claimed is:

1. A dry granulation process for manufacturing a pharmaceutical composition having uniform drug distribution and potency, the process comprising in the following order the steps of:

(1) blending silicon dioxide and at least one pharmaceutically acceptable excipient, carrier or diluent in a high shear granulator for an appropriate amount of time to produce a blended mixture;

(2) adding an active ingredient to the granulator and blending for an additional period of time to form an active blend;

(3) transferring the active blend from the granulator to a blender;

(4) optionally, adding one or more additional pharmaceutically acceptable excipients, carriers or diluents to the active blend; and (5) blending for a suitable period of time to form a pharmaceutical composition having uniform distribution of the active ingredient and uniform potency, wherein said active ingredient is a compound of Formula (I)

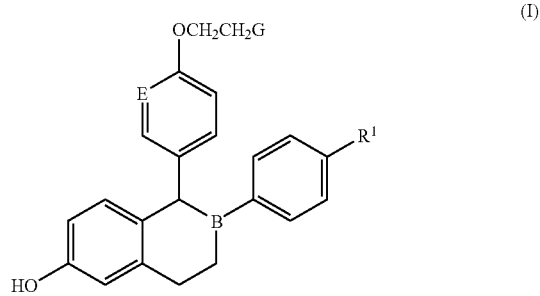

where E and B are independently selected from CH and N; $R^1$ is hydrogen, hydroxy, fluoro or chloro; and G is

or a pharmaceutically acceptable salt, hydrate or solvate of said compound.

2. The dry granulation process of claim 1 wherein said active ingredient is selected from the group consisting of cis-6-(4-fluoro-phenyl)-5-[4-(2-piperidin-1-yl-ethoxy)-phenyl]-5,6,7,8-tetrahydro-naphthalen-2-ol; (−)-cis-6-phenyl-5-[4-(2-pyrrolidin-1-yl-ethoxy)-phenyl]-5,6,7,8-tetrahydro-naphthalen-2-ol; cis-6-phenyl-5-[4-(2-pyrrolidin-1-yl-ethoxy)-phenyl]-5,6,7,8-tetrahydro-naphthalen-2-ol; cis-6-(4-hydroxyphenyl)-5-[4-(2-piperidin-1-yl-ethoxy)-phenyl]-5,6,7,8-tetrahydro-naphthalen-2-ol; and 1-(4'-pyrrolidinolethoxyphenyl)-2-phenyl-6-hydroxy-1,2,3,4-tetrahydroisoquinoline;, or a pharmaceutically acceptable salt, hydrate or solvate of said compound.

3. The dry granulation process of claim 2 wherein said active ingredient is (−)-cis-6-phenyl-5-[4-(2-pyrrolidin-1-ylethoxy)phenyl]-5,6,7,8-tetrahydronaphthalen-2-ol, or a pharmaceutically acceptable salt, hydrate or solvate of said compound.

4. The dry granulation process of claim 3 wherein said active ingredient is a D-tartrate salt of (−)-cis-6-phenyl-5-[4-(2-pyrrolidin-1-ylethoxy)phenyl]-5,6,7,8-tetrahydronaphthalen-2-ol.

5. The dry granulation process of claim 1, 2, 3 or 4 further comprising the step of processing said pharmaceutical composition into a unit dosage form.

6. The dry granulation process of claim 5 wherein said active ingredient is present in said unit dosage form in amount from about 0.01 mg to about 10.0 mg.

7. The dry granulation process of claim 5 wherein said active ingredient is present in said unit dosage form in an amount from about 0.05 mg to about 5.0 mg.

8. The dry granulation process of claim 5 wherein said active ingredient is present in said unit dosage form in an amount between about 0.05 mg and about 4.0 mg.

9. The dry granulation process of claim 5 wherein said active ingredient is present in said unit dosage form in an amount between about 0.1 mg and about 3.5 mg.

10. The dry granulation process of claim 5 wherein said active ingredient is present in said unit dosage form in an amount between about 0.1 mg and about 2.5 mg.

11. The dry granulation process of claim 5 wherein said silicon dioxide is present in an amount from about 0.1% to about 2% by weight of said unit dosage form.

12. The dry granulation process of claim 5 wherein said silicon dioxide is present in an amount from about 0.15% to about 1.0% by weight of said unit dosage form.

13. The dry granulation process of claim 5 wherein said silicon dioxide is present in an amount from about 0.25% to about 0.75% by weight of said unit dosage form.

14. The dry granulation process of claim 1 wherein, in step (1) the blending of silicon dioxide and at least one pharmaceutically acceptable excipient, carrier or diluent in a high shear granulator is carried out for about 5 minutes to form a blended mixture; in step
  (2) the active ingredient is blended for about 10 minutes to about 15 minutes to form an active blend; and in step
  (4) optionally, adding one or more additional pharmaceutically acceptable excipients, carriers or diluents to the active blend; and in step
  (5) blending for about 5 minutes to about 15 minutes to form a pharmaceutical composition having uniform distribution of the active ingredient and uniform potency.

15. A pharmaceutical composition prepared by the method of claim 1, 2, 3, 4, or 14.

16. A medicament prepared by a dry granulation process, the process comprising in the following order the steps of:
  (1) blending silicon dioxide and at least one pharmaceutically acceptable excipient, carrier or diluent in a high shear granulator for an appropriate amount of time to produce a blended mixture;
  (2) adding an active ingredient to the granulator and blending for an additional period of time to form an active blend;
  (3) transferring the active blend from the granulator to a blender;
  (4) optionally, adding one or more additional pharmaceutically acceptable excipients, carriers, or diluents to the active blend;
  (5) blending for a suitable period of time to form a pharmaceutical composition having uniform distribution of the active ingredient and uniform potency; and
  (6) processing said pharmaceutical composition into a unit dosage form,
wherein said active ingredient is a compound of Formula (I)

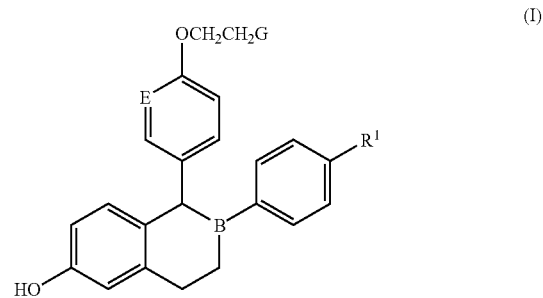

where E and B are independently selected from CH and N; $R^1$ is hydrogen, hydroxy, fluoro or chloro; and G is

or a pharmaceutically acceptable salt, hydrate or solvate of said compound.

17. The medicament of claim 16 wherein said active ingredient is a compound selected from the group consisting of cis-6-(4-fluoro-phenyl)-5-[4-(2-piperidin-1-yl-ethoxy)-phenyl]-5,6,7,8-tetrahydro-naphthalen-2-ol; (−)-cis-6-phenyl-5-[4-(2-pyrrolidin-1-yl-ethoxy)-phenyl]-5,6,7,8-tetrahydro-naphthalen-2-ol; cis-6-phenyl-5-[4-(2-pyrrolidin-1-yl-ethoxy)-phenyl]-5,6,7,8-tetrahydro-naphthalen-2-ol; cis-6-(4-hydroxyphenyl)-5-[4-(2-piperidin-1-yl-ethoxy)-phenyl]-5,6,7,8-tetrahydro-naphthalen-2-ol; and 1-(4'-pyrrolidinolethoxyphenyl)-2-phenyl-6-hydroxy-1,2,3,4-tetrahydroisoquinoline; or a pharmaceutically acceptable salt, hydrate or solvate of said compound.

18. The medicament of claim 17 wherein said compound is (−)-cis-6-phenyl-5-[4-(2-pyrrolidin-1-ylethoxy)phenyl]-5,6,7,8-tetrahydronaphthalen-2-ol; or a pharmaceutically acceptable salt, hydrate or solvate of said compound or said prodrug.

19. The medicament of claim 18 wherein said compound is a D-tartrate salt of (−)-cis-6-phenyl-5-[4-(2-pyrrolidin-1-ylethoxy)phenyl]-5,6,7,8-tetrahydronaphthalen-2-ol.

20. The medicament of claim 16 wherein said active ingredient is present in said unit dosage form in an amount from about 0.01 mg to about 10.0 mg.

21. The medicament of claim 16 wherein said active ingredient is present in said unit dosage form in an amount from about 0.05 mg to about 5.0 mg.

22. The medicament of claim 16 wherein said active ingredient is present in said unit dosage form in an amount between about 0.05 mg to about 4.0 mg.

23. The medicament of claim 16 wherein said active ingredient is present in said unit dosage form in an amount between about 0.1 mg to about 3.5 mg.

24. The medicament of claim 16 wherein said active ingredient is present in said unit dosage form in an amount between about 0.1 mg to about 2.5 mg.

25. The medicament of claim 16 wherein said silicon dioxide is present in an amount from about 0.1% to about 2% by weight of said unit dosage form.

26. The medicament of claim 16 wherein said silicon dioxide is present in an amount from about 0.15% to about 1.0% by weight of said unit dosage form.

27. The medicament of claim 16 wherein said silicon dioxide is present in an amount from about 0.25% to about 0.75% by weight of said unit dosage form.

* * * * *